US012755849B2

(12) United States Patent
Jutla et al.

(10) Patent No.: US 12,755,849 B2
(45) Date of Patent: Oct. 6, 2026

(54) PREDICTIVE MODELS FOR INFECTIOUS DISEASES

(71) Applicants: University of Florida Research Foundation, Inc., Gainesville, FL (US); University of Maryland, College Park, College Park, MD (US)

(72) Inventors: Antarpreet S. Jutla, Gainesville, FL (US); Moiz Usmani, Gainesville, FL (US); Rita Colwell, College Park, MD (US)

(73) Assignees: University of Florida Research Foundation, Inc., Gainesville, FL (US); University of Maryland, College Park, College Park, MD (US)

( * ) Notice: Subject to any disclaimer, the term of this patent is extended or adjusted under 35 U.S.C. 154(b) by 187 days.

(21) Appl. No.: 18/374,237

(22) Filed: Sep. 28, 2023

(65) Prior Publication Data

US 2024/0029894 A1 Jan. 25, 2024

Related U.S. Application Data

(63) Continuation of application No. PCT/US2022/071287, filed on Mar. 23, 2022.

(Continued)

(51) Int. Cl.

*G16H 50/30* (2018.01)
*G16H 50/50* (2018.01)
*G16H 50/80* (2018.01)

(52) U.S. Cl.

CPC ............ *G16H 50/30* (2018.01); *G16H 50/50* (2018.01); *G16H 50/80* (2018.01)

(58) Field of Classification Search

CPC ........ G16H 50/80; G16H 50/70; G16H 50/30; G16H 50/20; G16H 50/50

See application file for complete search history.

(56) References Cited

U.S. PATENT DOCUMENTS 11,127,506 B1 * 9/2021 Jain ....................... H04W 4/021
11,504,011 B1 * 11/2022 Jain .......................... G06N 5/04

(Continued)

OTHER PUBLICATIONS

Woolhouse M. How to make predictions about future infectious disease risks. Philos Trans R Soc Lond B Biol Sci. Jul. 12, 2011;366(1573):2045-54. doi: 10.1098/rstb.2010.0387. PMID: 21624924; PMCID: PMC3130384 (Year: 2011).*

(Continued)

*Primary Examiner* — Joseph D Burgess

(74) *Attorney, Agent, or Firm* — Thomas | Horstemeyer, LLP

(57) ABSTRACT

The present disclosure provides systems and methods for predicting the occurrence of an outbreak of an infectious disease. One such method includes acquiring environmental risk factor data associated with a particular disease, wherein the environmental risk factor data corresponds to a particular geographic region; acquiring social risk factor data associated with the particular disease; applying a prediction algorithm to the environmental and social risk factor data to generate a disease risk model for generating at least a trigger prediction and a transmission prediction for a disease-causing pathogen at the particular geographic region; generating the trigger prediction by applying the disease risk model to a forecast of data for a first lead time for the particular geographic region; and/or generating the transmission prediction by applying the disease risk model to the transmission prediction for a second lead time for the particular geographic region. Other methods and systems are also provided.

20 Claims, 6 Drawing Sheets

Related U.S. Application Data

(60) Provisional application No. 63/302,320, filed on Jan. 24, 2022, provisional application No. 63/168,060, filed on Mar. 30, 2021.

(56) References Cited

U.S. PATENT DOCUMENTS

| | | | | |
|---|---|---|---|---|
| 2009/0216860 | A1* | 8/2009 | Li | H04L 69/329<br>709/219 |
| 2012/0004111 | A1 | 1/2012 | Colwell et al. | |
| 2017/0103172 | A1* | 4/2017 | Fink | G16H 50/20 |
| 2017/0351831 | A1* | 12/2017 | Cahan | G06T 11/206 |
| 2019/0355480 | A1* | 11/2019 | Goodall | G16H 50/80 |
| 2021/0050116 | A1* | 2/2021 | Sabeti | G06N 7/01 |

OTHER PUBLICATIONS

International Search Report and Written Opinion mailed on Jun. 2, 2022 for PCT Patent Application PCT/US2022/071287. Copy Attached.

* cited by examiner

PREDICTIVE MODELS FOR INFECTIOUS DISEASES

CROSS-REFERENCE TO RELATED APPLICATION

This application is a continuation of PCT Application No. PCT/US2022/071287, filed on Mar. 23, 2022, which is entirely incorporated herein by reference, and claims priority to U.S. provisional application entitled, "Predictive Algorithms for Infectious Diseases," having Ser. No. 63/168,060, filed Mar. 30, 2021, which is entirely incorporated herein by reference, and claims priority to co-pending U.S. provisional application entitled, "Predictive Models for Infectious Diseases," having Ser. No. 63/302,320, filed Jan. 24, 2022, which is entirely incorporated herein by reference.

STATEMENT REGARDING FEDERALLY SPONSORED RESEARCH OR DEVELOPMENT

This invention was made with government support under Contract awarded by the National Aeronautics and Space Administration (NASA). The government has certain rights in the invention.

TECHNICAL FIELD

The present disclosure is generally related to a system and method for predicting the occurrence of an outbreak of an infectious disease.

BACKGROUND

Because outbreaks of diseases caused by pathogens (water, air or vector-borne) will continue to occur over time, the most effective means of controlling or preventing outbreaks is to minimize exposure to pathogenic strains by populations of people and/or high concentrations of pathogens. Accordingly, there is a need for predictive tools that can identify geographic locations that are susceptible to pathogen outbreaks at a future date.

SUMMARY

Embodiments of the present disclosure provide methods and related systems for predicting the occurrence of an outbreak of an infectious disease at a particular geographic location at a future date. Briefly described, one embodiment of the method, among others, includes acquiring, by a computing device, environmental risk factor data associated with a particular disease, wherein the environmental risk factor data corresponds to a particular geographic region; acquiring, by the computing device, social risk factor data associated with the particular disease, wherein the social risk factor corresponds to the particular geographic region; applying, by the computing device, a prediction algorithm to the environmental and social risk factor data to generate a disease risk model for generating at least a trigger prediction and a transmission prediction for a disease-causing pathogen at the particular geographic region; wherein the trigger prediction is a prediction of a disease outbreak at the particular geographic region; wherein the transmission prediction is a prediction of a human-to-human transmission of the disease-occurring pathogen at the particular geographic region; generating, by the computing device, the trigger prediction by applying the disease risk model to a forecast of data for a first lead time for the particular geographic region; and/or generating, by the computing device, the transmission prediction by applying the disease risk model to the transmission prediction for a second lead time for the particular geographic region.

The present disclosure can also be viewed as providing related systems. One such system comprises at least one processor and memory configured to communicate with the at least one processor, wherein the memory stores instructions that, in response to execution by the at least one processor, cause the at least one processor to perform operations comprising: acquiring environmental risk factor data associated with a particular disease, wherein the environmental risk factor data corresponds to a particular geographic region; acquiring social risk factor data associated with the particular disease, wherein the social risk factor corresponds to the particular geographic region; applying a prediction algorithm to the environmental and social risk factor data to generate a disease risk model for generating at least a trigger prediction and a transmission prediction for a disease-causing pathogen at the particular geographic region; wherein the trigger prediction is a prediction of a disease outbreak at the particular geographic region; wherein the transmission prediction is a prediction of a human-to-human transmission of the disease-occurring pathogen at the particular geographic region; generating the trigger prediction by applying the disease risk model to a forecast of data for a first lead time for the particular geographic region; and/or generating the transmission prediction by applying the disease risk model to the transmission prediction for a second lead time for the particular geographic region.

In one or more aspects of the system/method, the operations further comprise generating a risk map, wherein a trigger prediction score and a transmission prediction score are computed for a plurality of pixels of the risk map, wherein the plurality of pixels correspond to at least the particular geographic region.

In one or more aspects of the system/method, the forecasted data comprises a weather forecast for the particular geographic region; the first lead time or the second lead time comprises at least three weeks in the future; the environmental risk factor data comprises precipitation, air temperature, dew point temperature, air quality, sunlight, salinity, relative humidity, sea surface temperature, coastal location, or nutrients data; the environmental risk factor data comprises precipitation, air temperature, dew point temperature, air quality, sunlight, salinity, relative humidity, sea surface temperature, coastal location, or nutrients data; the social risk factor data comprises human mobility, population density, water infrastructure, economic stability, age demographic, population diversity, housing conditions, sanitation infrastructure, or behavioral data for the particular geographic region; the particular disease comprises cholera; the particular disease comprises COVID-19; and/or the particular disease-causing pathogen comprises a virus, bacteria, fungi, or a parasite.

Other systems, methods, features, and advantages of the present disclosure will be or become apparent to one with skill in the art upon examination of the following drawings and detailed description. It is intended that all such additional systems, methods, features, and advantages be included within this description and be within the scope of the present disclosure.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
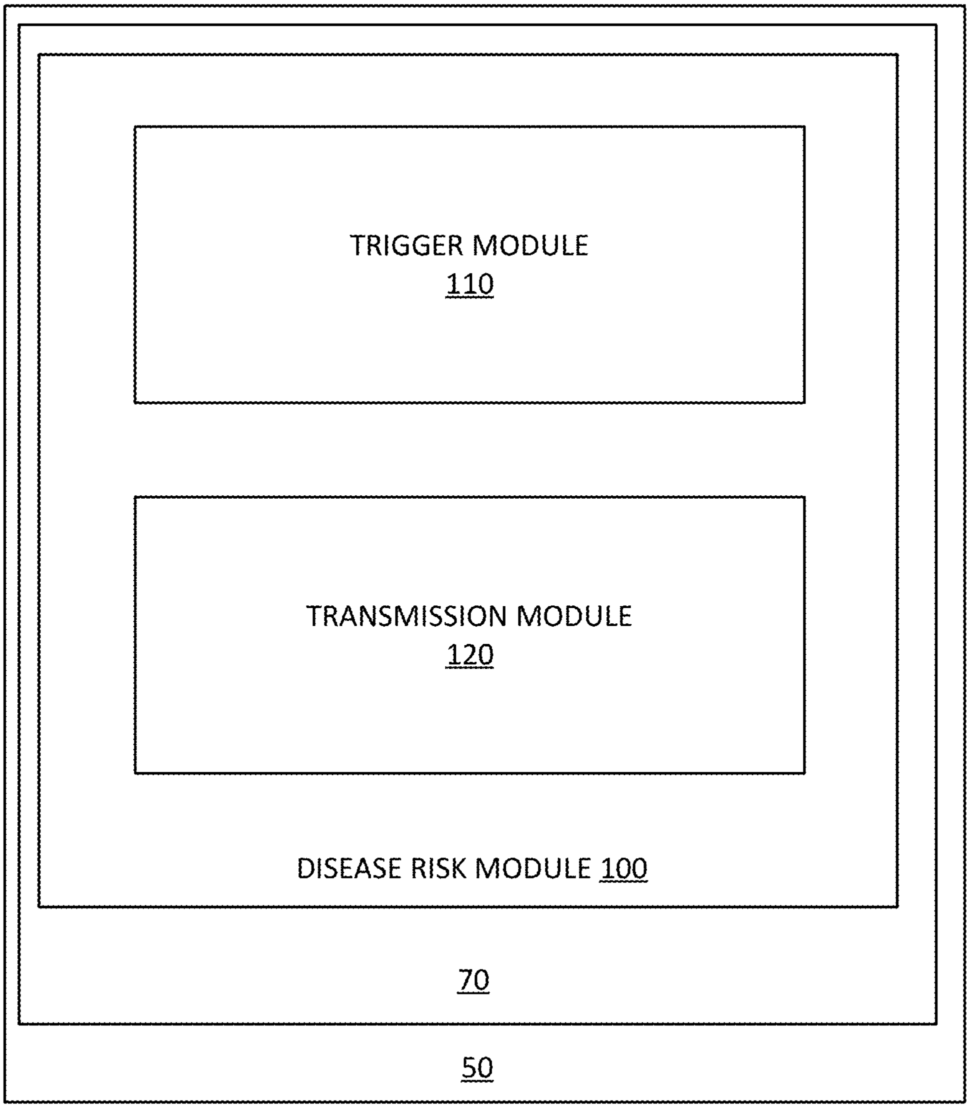
FIG. 1 shows a framework for an exemplary disease risk model in accordance with embodiments of the present disclosure.

The present disclosure describes various embodiments of systems, apparatuses, and methods for predicting the occurrence of an outbreak of an infectious disease at a particular geographic location at a future date, such as diseases involving pathogens that can spread via indirect contact with persons (e.g., air-borne transmissions, water-borne transmissions, vector-borne transmissions, etc.).

Systems and methods of the present disclosure are customizable to a host of infectious pathogens (e.g., viruses, bacteria, fungi, parasites, etc.) and interact with the human population to produce risk scores that enable for the categorization of likelihood of an outbreak risk in distinct categories (e.g., High, Medium, Low). The risk score approach is fundamentally different from traditional methods to understand how an outbreak of disease is likely to occur in the human population. The risk scores minimize disease surveillance data availability requirements (such as incidence/prevalence) and apply to global scales with little to no tweaking of model parameters. A motivation to use the score, rather than prevalence or incidence, is to be able to circumvent the lack of epidemiological data during public health emergencies, as is often a challenge due to lack of disease surveillance networks. The disclosed technology can provide information on when and where a potential water-, air-, and/or vector-borne disease outbreak will likely happen at a future date. In various embodiments, a key idea is the identification of a critical lead time (usually at least a few weeks) that will allow the development of mitigation and intervention plans to be in place to reduce the impacts of disease outbreaks.

In accordance with various embodiments, an exemplary system and method utilizes a disease risk model (DRM) that is an integrated platform that calculates the risk of the trigger (initiation risk of disease in population) and transmission (spread of disease in human population) of a particular infectious disease for a designated period or lead time in the future. As an example, a disease risk model for cholera can have a validity period of four weeks from the date of issue. In risk modelling, these lead times can be evaluated in terms of temporality since risk precedes incidence of disease. In the case of cholera, a lead time of five weeks can provide ample time for intervention and mobilization of resources. Cholera cases are generally observed four weeks after anomalous warm temperatures followed by anomalous high precipitation in those locations where there is significant deviation in the behavior of the population with respect to water use habits caused by damaged WASH infrastructure.

In various embodiments, the DRM is based on the integration of environmental and social risk factors, such as rainfall or precipitation (environmental), air temperature (environmental), dew point temperature (environmental), air quality (environmental), sunlight (environmental), salinity (environmental), relative humidity (environmental), sea surface temperature (environmental), coastal location (environmental), nutrients (environmental), and social determinants, such as human mobility via GPS tracking (social), population density (social), water security or infrastructure (social), economic stability (social), age demographics (social), population diversity (social), housing conditions (social), and access to water and sanitation infrastructure (social), cultural or behavioral norms (social), among others.

As described herein, a prediction system refers to a system that applies a prediction algorithm to data in order to generate a prediction model for making predictions. A prediction system can be a prediction server that applies the prediction algorithm and performs the related methods, wherein the prediction server comprises a digital processing device comprising at least one processor, an operating system configured to perform executable instructions, a memory, and a computer program including instructions executable by the digital processing device to create a server application.

As used herein, "variable" refers to a parameter used within a prediction model. As used herein, "average" refers to a statistical measure of a plurality of values. Average may refer to mean, median, mode, and range. As used herein, "risk" refers to the likelihood of occurrence of an event, such as a disease outbreak. A "risk prediction" refers to the likelihood of occurrence of an event, such as a disease outbreak. A risk prediction is calculated using a prediction model generated by a prediction algorithm. The prediction algorithm may involve comparing historical data involving pathogenic outbreaks and/or transmissions with historical data on environmental and/or social conditions and events in order to generate a prediction model that correlates the relationship between environmental and/or social conditions with the occurrence and/or spread of pathogenic diseases. The prediction algorithm may also comprise machine learning methods in generating the prediction model. A prediction model can be a formula comprising parameters that determine the likelihood of a defined event. For example, a prediction model can be a multiple linear regression model or formula, a classifier, and/or trained algorithm generated by the application of a machine learning algorithm to a dataset comprising epidemiological, environmental, and/or social data.

In various embodiments, a prediction system involves a prediction server 50 that executes a software application 70 having a framework for a prediction model in the form of a disease risk module 100 that is divided into a trigger module 110 and a transmission module 120), as represented in FIG. 1. The trigger module 110 outputs a prediction of a risk associated with an outbreak of a disease being introduced within a human population at a particular geographic location and the transmission module outputs a prediction of a risk associated with the disease being transmitted through human-to-human transmission of the disease as opposed to the outbreak (that is predicted by the trigger module). In general, the trigger module 110 uses environmental and social risk factors (e.g., data on precipitation, temperature, population, sanitation infrastructure, etc.) to compute a risk score with values that vary between 1 (high) and 0 (low) in a given region. The trigger algorithm identifies conditions of anomalous temperature and rainfall, providing an assessment of disease risk for a window of time in the future, such as, but not limited to, the following four-five weeks for a given region and disease.

Accordingly, in various embodiments, the transmission module 120 can be used in conjunction with the trigger module 110 to provide assessment and output a prediction on "given a trigger risk X, the corresponding transmission risk is likely to be Y." In various embodiments, output from the trigger module 110 and/or transmission module 120 of the DRM is a risk score at a resolution of 1 km×1 km, with predicted risk ranging from high (numerical value of 1) to low (numerical value of 0). Once the risk scores are generated at 1 km resolution, it can be averaged over a user specified area of interest.

It is noted that most conventional epidemiological models and modeling algorithms are based on compartmentalized susceptible-infected-recovered (SIR) type of approaches. The basic idea of SIR models is to compute the theoretical number of people infected with a contagious illness over time and how the disease spread through a given population using various parameters. SIR models usually start with the premise that pathogens are transmitted via human to human interaction. Studies have highlighted the role of environmental conditions for creating seasonality in certain diseases but have not elaborated on plausible physical or social mechanisms related to seasonality of outbreaks. There are regressive models (using regression techniques) for associating incidence/prevalence of diseases like cholera with various environmental factors. However, these regressive models also do not possess prediction capabilities. In the epidemiological domain, there is less familiarity with the concept of using forecasted risk of disease outbreak to take early action, even though there are several diseases which are associated with environmental factors which may offer a means for predicting risk. This is primarily because of a lack of disciplinary focus on the integration of weather and climate information with epidemiological data. This, in part, can be attributed to the absence of predictive tools for diarrheal disease, such as cholera.

DRM models of the present disclosure are hypothesis driven, meaning that we are using a physically plausible explanation to derive a model structure. Our models are predictive in nature, whereas most of the models in literature (epidemiological/medical) are simulative, implying that they can generate "what if" type of scenarios. Prediction implies forecasting a true unknown. An exemplary modeling scheme is similar to weather forecasting where the future is uncertain, but based on our physical understanding on how pathogens grow and survive, a risk of a disease outbreak (e.g., cholera, COVID-19, etc.) can be predicted. While most conventional models simulate (or require) disease prevalence or incidence time series, an exemplary model of the present disclosure does not require disease prevalence or incidence time series and can provide a risk score (e.g., between 0 and 1) defining the likelihood of disease outbreak. Further, since DRM is a hypothesis driven model, it does not require calibration unlike traditional disease simulation models. In various embodiments, the risk score can be presented in one or more risk maps indicating a likelihood of an outbreak and/or human-to-human transmission of a particular disease to occur based on environmental and social factors for a date in the future (e.g., three to four weeks in the future).

In various embodiments, an exemplary software application 70 for predicting a disease can include a plurality of modules (in addition to the trigger and transmission modules) for respective environmental and social risk factors, where each of the module's dataset is provided a weight. Based on the disease being evaluated, certain variables may be more relevant to others and therefore their associated weights will be given greater values. In the case of cholera, as a non-limiting example, one module may have precipitation as one of the variables for disease prediction. In various embodiments, a long term precipitation average may then be taken (e.g., mean of 30 years of data), and the mean can be subtracted from the current month's value to get an anomaly. The anomaly is then given a weight based on standard deviation of the dataset. Each of the modules' weights may then be added and rescaled to obtain a value between 0 and 1. For example, in various implementations, monthly anomalies (defined as a departure from an average condition) use Equation 1, where MA=Monthly Anomaly, MV=Monthly Value, LTAV=Long Term Average Value:

$$MA = MV_{Precipitation/Temperature} - LTAV_{Precipitation/Temperature}. \quad (1)$$

For illustration purposes, to calculate air temperature anomalies for a given month (e.g., September), an average for monthly data from 1981 to 2016 may be determined and subtracted from the value for the corresponding month of year 2016. The resulting positive value (anomaly) implies that the month is warmer, based on the historical mean condition and vice versa. For estimation of a precipitation anomaly for a given month, an average monthly data value may be estimated using Tropical Rainfall Measuring Mission (TRMM) data and subtracted from the corresponding monthly Global Precipitation Mission (GPM) value for year 2016. As was determined for air temperature, a positive precipitation anomaly implies a wetter month, compared with the historical mean condition and vice versa. For a region of interest, these anomalies can be calculated for both monthly total precipitation and monthly mean air temperature, covering all pixels over the region of interest.

The relative weight of each variable can be assigned a risk level, e.g., very high, high, moderate, low, or very low, where the weight value corresponds to the risk indicated by the environmental and/or social factors for a particular region. Accordingly, anomaly thresholds can be set that determine how weights are assigned, where the thresholds can be adapted based on the factors associated with a particular region.

Existing prediction models, such as probabilistic weather forecasting, are able to predict environmental variables, such as weather, to a reasonable accuracy, especially within a 24-48 hour time window. The systems and methods of the present disclosure apply a prediction algorithm to environmental and social information to build one or more prediction models (e.g., DRM) and for entering relevant data (model parameters) into the models to generate risk predictions of future disease outbreaks/transmissions within a time window (e.g., two-four week time window, etc.). For example, in the case of COVID-19, regions having large population densities are positively correlated with an outbreak of COVID-19. Consider that regions with population densities greater than 5000 people per square mile in the United States have about 95% probability of COVID-19 transmission. Further, high and/or low ambient air and dew point temperatures have also been positively correlated with COVID-19 outbreaks in some studies. Correspondingly, in another non-limiting example, extreme air temperatures and rainfall conditions in combination with poor water sanitation conditions within a particular geographic region have been positively correlated with an outbreak for cholera, and a prediction model can account for these relationships.

In brief, cholera has been defined as occurring in two dominant forms: (1) Epidemic which is characterized by sudden and sporadic occurrence of a large number of cases, and (2) Endemic where cholera cases occur at a baseline level throughout the year, with distinct seasonal peaks. Epidemic cholera is hypothesized to be related to elevated air temperatures followed by above average precipitation, in concatenation with insufficient and/or damaged water, sanitation, and hygiene (WASH) infrastructure. Endemic cholera is associated with a constant occurrence of cholera cases, primarily in regions where coastal or terrestrial water systems create favorable conditions for growth and proliferation of *Vibrio cholerae*. Under certain environmental conditions, a sustained epidemic mode of cholera can evolve into the endemic form in regions where there is enhanced and continuing exposure to, and transmission of, *Vibrio cholerae*. If cholera is becoming endemic, the transmission mode of the DRM may be more relevant than the trigger mode as the transmission mode predicts the human-to-human transmission of the disease as opposed to the outbreak.

Cholera is transmitted by drinking water contaminated with infective doses of the pathogenic vibrio's, especially when the water resources are compromised, leading to enhanced interaction of humans with the pathogen. Therefore, in addition to the presence of a susceptible human population, the availability of a WASH infrastructure can be taken into account to calculate a realistic risk of cholera in a region.

Analysis of the epidemiological data shows cholera risk can be predicted successfully by employing environmental and epidemiological factors, including precipitation (Hashizume et al., 2008); flooding (Koelle et al., 2005); sea surface temperature and height (Lobitz et al., 2000); river level and freshwater discharge (Akanda et al., 2011; Schwartz et al., 2006); coastal salinity (Miller et al., 1982); dissolved organic material (Neogi et al., 2018); chlorophyll (Constantin de Magny et al., 2008), and components of phytoplankton and zooplankton (Constantin de Magny et al., 2008; de Magny et al., 2011). Epidemiological surveillance suggests a link with estuarine ecosystems, namely river and coastal regions (Lipp et al., 2002). Additionally, disease predictions can be achieved by recognizing that disease progression comprises two components: trigger and transmission. These, together, result in an outbreak and, subsequently, a public health emergency.

As such, rainfall can have a significant impact on a water resource, e.g., nutrient concentration, salinity, pH, river level, and freshwater discharge, which in turn affect growth and persistence of *Vibrio cholerae* and its zooplankton host in the environment. Various studies have determined dependence of air temperature and precipitation as dominant hydroclimatic variables impacting occurrence and transmission of cholera in various parts of the world. Following creation of the disease risk model (DRM), knowledge of upcoming weather forecasts in a geographic area and/or current or forecasted social conditions (e.g., an area has poor sanitation or is forecasted to have a setback in sanitation capabilities) can be entered into the DRM to generate one or more risk predictions for cholera, as an illustrative and non-limiting example. For example, in the case of cholera, damaged WASH infrastructure accelerates interaction between *Vibrio cholerae*, thereby enhancing characteristics of the available water resource, notably lack of safe water, sanitation, and hygiene, increasing the likelihood of water-borne disease in the population.

The trigger module 110 is designed to capture disease initiation in a region; therefore, unless there are new outbreak(s), the model performance should decline over the years since transmission dynamics, as captured by the transmission module 120, should dictate spread of the particular disease in a human population.

The systems, methods, and media of the present disclosure can issue status updates (e.g., warnings) of elevated risk for specified diseases based on risk predictions. The status updates may be sent specifically to subjects or individuals who are within the scope of the risk prediction (e.g. located within the defined geographic area during the defined time period). Updates may be sent to the communication devices of one or more subjects with the goal of providing pre-emptive warning to potentially prevent these situations from occurring at all. Updates may be sent automatically whenever a risk prediction exceeds a defined risk threshold. In various embodiments, the updates can be communicated to communication devices over data communication channels, for example, Internet, Web, or Email channels. The updates may be sent from a prediction server. In certain scenarios, output from the prediction server may be presented in an electronic (e.g., PDF) document which can be sent as an attachment to an email message. In other situations, accessing the prediction server through a web-portal may be beneficial and improve access to the tool and enable users to interact with its outputs more flexibly. Such a web-based tool can act as a dashboard which enables decision makers to see an overview of an outbreak risk and a regional/global level to identify potential hotspots. Accordingly, access via a smartphone app to display risk assessments may also be beneficial in certain implementations. However, in certain area, access to the Internet may be limited. Thus, providing a variety of options for accessing the prediction server will help to tailor the service to the needs of individual users.

In an exemplary implementation, updates may be communicated to an Emergency Operation Center which maintains a table/report of districts most affected by a particular disease strain, such as cholera. Accordingly, in the case of cholera, DRM risk scores and rainfall forecasts can be considered alongside this data. Exemplary rainfall forecasts may provide rainfall information to users on a weekly basis. This includes a 7-day hindcast, a 7-day forecast, a 4-week forward outlook, and a summary highlighting high impact weather. The forecasts may also include maps showing the spatial distribution of rainfall and tables giving forecast rainfall, by category, for specific locations around the applicable country. The districts may then be ranked into low-high risk categories according to where there are cases already and where predictions suggest these will increase. The most appropriate action to take in high-risk districts is then identified, based on local contexts.

The prediction server may comprise one or more computers that provide a disease risk prediction service. In some embodiments, the prediction server may comprise one or more servers and/or is hosted on the Internet or part of a network. Accordingly, the prediction server may be one or a group of computers. Each server computer may include several components such as at least one central processing unit or processor (CPU), an operating system configured to perform executable instructions, a memory unit, a network or communication element (e.g., an antenna and associated components, Wi-Fi, Bluetooth, etc.) and a computer program including instructions executable by the digital processing device or a software application for applying a prediction algorithm to environmental, social, and/or epidemiological data to create a prediction model for generating one or more risk predictions for disease outbreak/transmission. An interface (e.g. user interface) may display a map with graphical representations of risk predictions for defined geographic areas within the map during a defined time period for a particular disease. In various embodiments, a weighed raster overlay algorithm can be used to compute risk maps. In some embodiments, the risk prediction map may show areas of higher risk by use of a darker shade or a different color. In some embodiments, the risk probability may be compared to thresholds and determined that the risk is elevated.

The software application 70 for applying the prediction algorithm may comprise one or more modules, which may or may not be separable within the application or the list of instructions. The software application 70 may include one or more modules for obtaining different types of data from various sources for generating the risk prediction. The software application 70 may further include a disease risk module 100 for applying a prediction algorithm to the different types of data to generate disease risk model. The disk risk module 100 may apply the disease risk model (DRM) to current or forecasted data to generate a risk prediction across pixels of a map for one or more regions.

The software application 70 may be in any computer programming languages such as Perl, PHP, Python, Ruby, JavaScript (Node), Scala, Java, Go, ASP.NET, ColdFusion, etc. In some embodiments, the DRM module may use machine learning principles including Support Vector Machine (SVM), Random Forest (RF), Naive Bayes Classifier, neural networks, deep neural networks, logistic regression, etc., for classification. A prediction algorithm may comprise generating a disease risk model using machine learning on environmental and social data, wherein the machine learning is selected from Support Vector Machine (SVM), Random Forest (RF), Naive Bayes Classifier, neural networks, deep neural networks, and logistic regression.

In various embodiments, the software modules disclosed herein comprise a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application.

Figure 2:
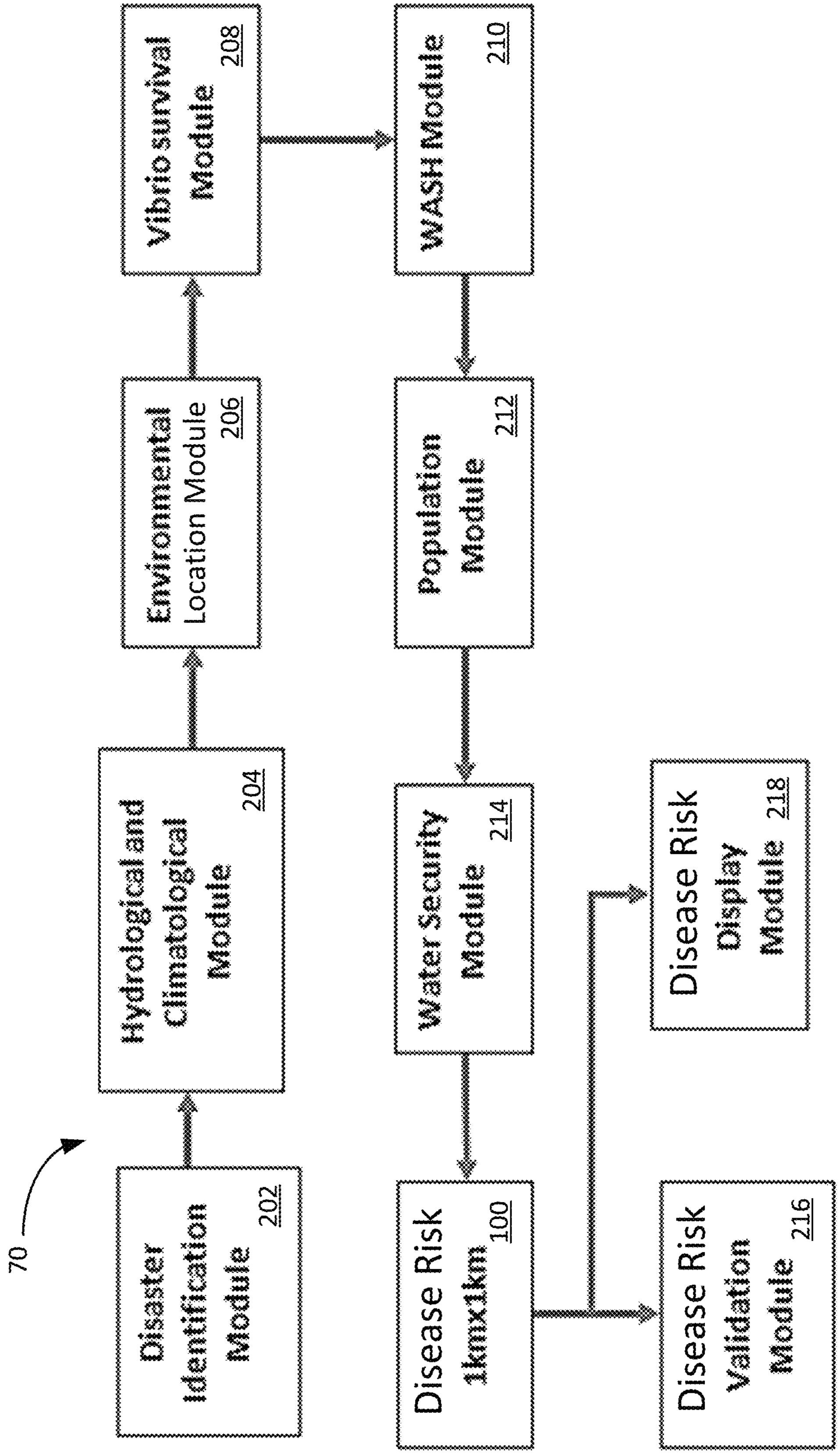
FIG. 2 shows a structure of an exemplary disease risk model for predicting cholera in accordance with embodiments of the present disclosure.

As an illustration, in the context of applying a prediction algorithm for cholera, FIG. 2 shows a structure of an exemplary software application 70 for predicting cholera that includes 8 modules or routines. In various embodiments, an exemplary prediction algorithm may start with a module 202 for acquiring data involving identification of a major disaster event (man-made or natural) which is input to a hydrological and climatological module 204 where a large scale assessment of regional conditions supporting vibrios (pathogens responsible for disease outbreak) is conducted. Natural disasters can have a significant effect on water resources that includes access to and availability of a safe drinking water supply in developing countries. The World Health Organization (WHO) defines natural disasters as "catastrophic events with atmospheric, geologic, and hydrologic origins." Such disasters include earthquakes, volcanic eruptions, storm surges, extreme temperatures, landslides, tsunamis, wildfires, floods, and droughts.

An environmental location module 206 can make an evaluation on possible locations of the vibrios given hydroclimatological conditions. In one embodiment, a vibrio survival module 208 was developed using about 40 years of data knowledge from University of Maryland. This is in form of a lookup table as a function of temperature and survival of vibrios under those conditions (Huq et al., 2005a). A WASH module 210 makes an evaluation on the availability of safe WAter, Sanitation, And Hygiene (WASH) infrastructure at the time prior and after the disaster event, where such information is routed to a population module 212. The population module 212 can evaluate the density of humans and locations of settlements in a region. In one embodiment, the population module dataset is derived from LandScan data managed by Oak Ridge National Lab in the USA. Water security module 214 can have information on where and when any intervention is being done so that outbreak of cholera can be stopped. Finally, the disease risk module 100 can combine the entire information and produces a risk value for disease outbreak and/or transmission. The advantage of using risk values instead of the actual case (prevalence or incidence) values is that the prediction algorithm becomes independent from the epidemiological data requirements. In other words, the algorithm does not require epidemiological data to produce the risk values. However, model outputs can be validated, via a validation module 216, once the epidemiological data becomes available and/or displayed via a display module 218. Different geographical regions will have different datasets available, therefore, depending on availability of data, the prediction model and number/types of modules used can be modified based on the available data.

An exemplary DRM can include data from a range of sources. As a non-limiting example, rainfall data can include daily and monthly rainfall data at two different resolutions, such as that obtained from the National Aeronautics and Space Administration (NASA). Monthly rainfall data, at a resolution of 0.25°×0.25° epidemiological from the Tropical Rainfall Measuring Mission (TRMM) can be employed to compute the long-term average (e.g. over a 10 year span). Daily rainfall data at a spatial resolution of 0.1°×0.1° may be obtained from the Global Precipitation Mission (GPM) and used to determine precipitation variation from long-term average at resampled data points. The average correlation over land between GPM and TRMM data is very high (>0.90) with small bias (unidirectional-negative bias) (Liu, 2016). An exemplary prediction server 50 can compute anomalies and thereafter bin or group the data based on standard deviation of TRMM datasets. Additionally or as an alternative source, satellite data can be used for rainfall observations or for other types of environmental conditions. Satellite derived observation data can be supplied by the NASA Global Precipitation Measurement dataset. Using satellite-derived data on precipitation, gridded air temperature, and hurricane path, changing environmental conditions conducive for growth of pathogenic vibrios can be tracked. As another example, cholera bacteria show strong association with plankton abundance in coastal ecosystems. Thus, remote sensing data can be used to track coastal plankton blooms, using chlorophyll as a surrogate variable for plankton abundance, and subsequent cholera outbreaks. Satellite data, with its unprecedented spatial and temporal coverage, have potentials to monitor coastal processes and track cholera outbreaks in endemic regions.

Accordingly, another data source may include air temperature, such as daily and monthly data for air temperature on the surface, at a spatial resolution of 0.5°×0.625°, which can be obtained from the NASA Modern-Era Retrospective analysis Research and Application, Version 2 (NASA-MERRA 2), and used to compute long-term averages and calculate anomalies. Population data in the form of LandScan population data at a spatial resolution of 1 km×1 km can be obtained from Oak Ridge National Laboratory and used in the DRM model. Epidemiological data can be used for validation and evaluation of model outputs.

Figure 3:
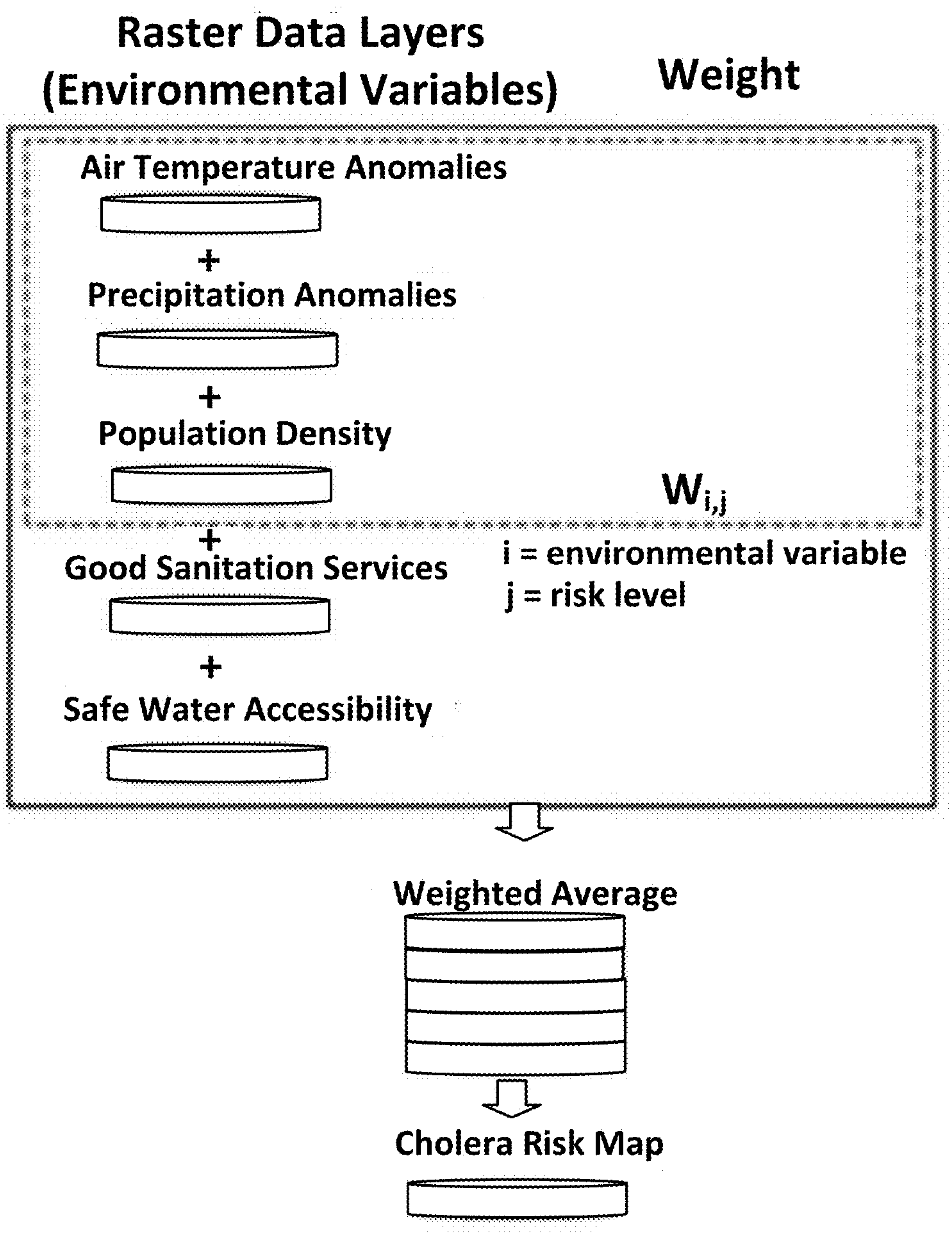
FIG. 3 shows a flowchart for developing a prediction risk map in accordance with embodiments of the present disclosure.
Figure 4:
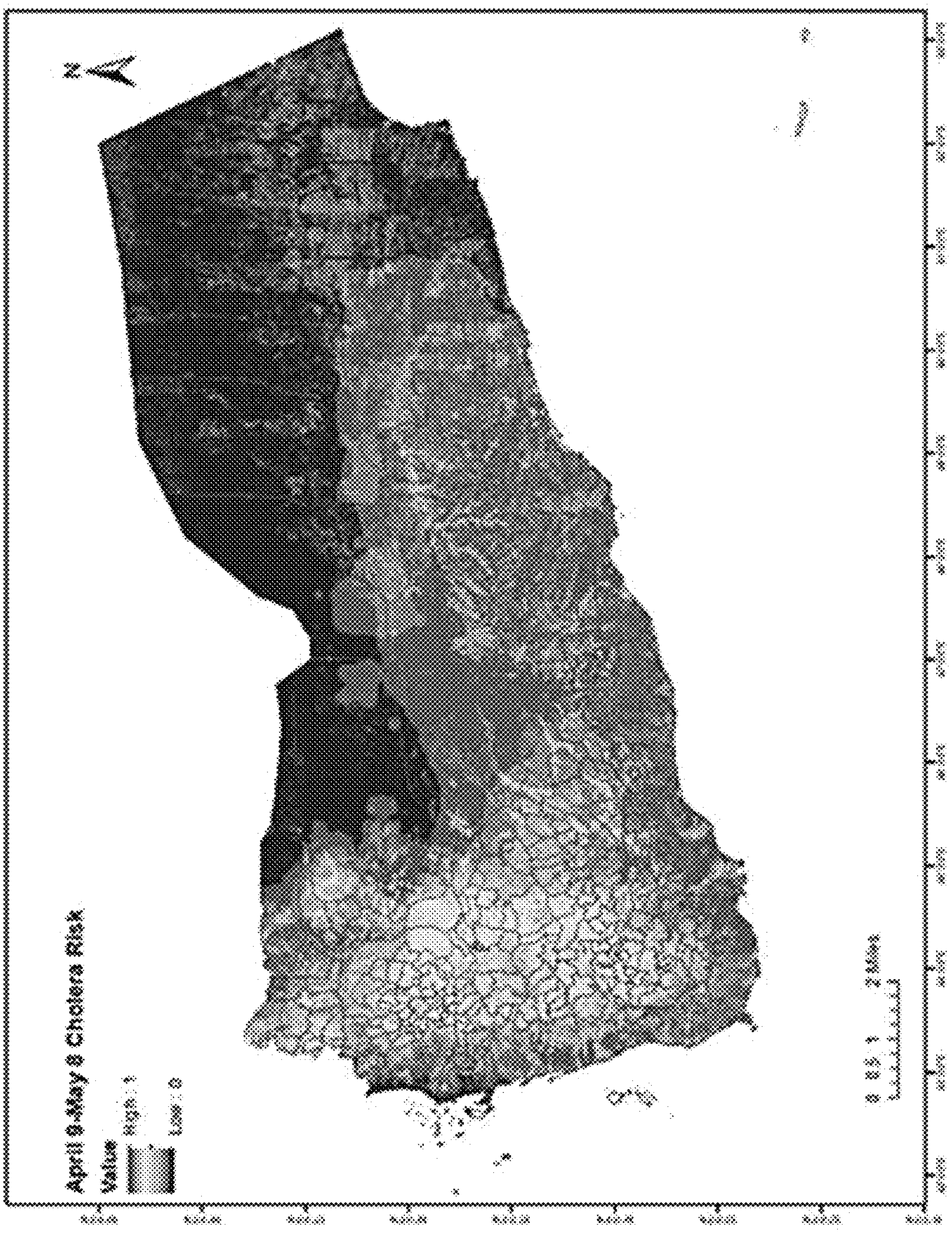
FIG. 4 shows an exemplary risk map in accordance with embodiments of the present disclosure.

In various embodiments, a weighted raster overlay algorithm can be used by a prediction server 50 to compute risk maps for cholera. Weighted raster overlay is a technique for applying a common measurement scale of values to diverse and dissimilar inputs to create an integrated output with attributable outcomes (e.g., high risk to low risk). FIG. 3 shows steps to apply this algorithm to develop cholera risk maps. The algorithm begins by selecting appropriate hydro-climatic and societal variables associated with the triggering of epidemic cholera. The dataset can include precipitation and air temperature anomalies, human population parameters, and hurricane wind swath and track. Each raster layer can be classified as a risk cluster and assigned an integer value based on a predefined evaluation scale (Table 1). The dotted box at the left represents layers used to generate a hydro-climatic risk map and the solid box incorporates the WASH infrastructure into the risk computation. An exemplary risk map is shown in FIG. 4.

TABLE 1

Risk classification for each layer

| Risk level | Precipitation anomalies (mm/day) | Temperature anomalies (° C.) | Population densities (count per km$^2$) | Wind swath of hurricane |
|---|---|---|---|---|
| Very high | 4 (>15) | 4 (>2) | 4 (>1,000) | 4 (closest to track point) |
| High | 3 (>5) | 3 (>1) | 3 (>500) | 3 |
| Moderate high | 2 (>3) | 2 (>0.5) | 2 (>250) | 2 |
| Low | 1 (>1) | 1 (0.25) | 1 (>25) | 1 |
| Very Low | 0 | 0 | 0 | 0 (outside wind swath) |

Accordingly, a population density layer along with two month's lagged monthly mean air temperature anomaly and one month lagged monthly total precipitation anomaly layers were used to produce the hydroclimatic risk map for likelihood of occurrence of cholera. Thereafter, information on regional water resources (WASH infrastructure) was added to the risk assessment. When applying the weighted raster overlay algorithm, input raster layers can be assigned an integer value or can be converted to an integer. Each input raster may be assigned a new value based on an evaluation scale (Table 1). The new values may be deemed to be a "reclassification" of the original input raster values. The evaluation scale can be determined based on the range of all raster layers for the variable under consideration. With respect to the illustrative example of Table 1, the air temperature anomaly evaluation scale was determined based on maximum and minimum values of the raster layers for all May, June, July anomalies. Every input raster was weighted according to importance (in terms of percent influence) and was converted to relative percentage; total being 100. Changing evaluation scales or percent influence can change the results in the final risk map. Different weights were computed while determining risk of cholera under various scenarios e.g. hydroclimatic and WASH based risk assessment. The relative weight of each variable was assigned a risk level, e.g. very high, high, moderate high, low, or very low. All weighted and classified raster layers were added to create a risk composite, representing the influence of each of the variables. Hydroclimatological departure from normal conditions was assumed to the strongest contributor to risk of cholera. Using each pair of precipitation and temperature anomalies, along with population density, composite maps of spatial cholera risk can be generated.

Improving understanding of the impact that inter-annual climate/environmental events such as El Niño and other seasonal patterns may have on cholera could enable even earlier indications of where cholera may be an issue. Paz (2019) has suggested that whilst the cause of the Yemeni cholera outbreak in 2017 is unclear, a combination of the impact of the strong El Niño of 2015-16 on cholera incidence in Somalia, followed by south-western winds over the Gulf of Aden throughout the summer of 2016, contributed to the disease spreading from the Horn of Africa to Yemen. If further research finds a significant correlation between inter-annual events like El Niño and cholera, early predictions (*forecasts) of El Niño can be used for longer-term decision planning and resource allocation. Improved understanding of inter-annual events on cholera could inform whether predictions for such events would be relevant for cholera responders.

As discussed, in the case of cholera, environmental factors are associated with cholera including precipitation along with other environmental and social factors (e.g. sanitation conditions), so there should be caution in using rainfall alone as a determinant of cholera. Rather, rainfall forecasts (or other reliable forecast related to relevant environmental and/or social risk factors) should be used alongside tools such as the DRM. Based on areas identified as being at high risk by having conditions susceptible to an outbreak or spreading of cholera in combination with a rain or storm event, rain forecasts can be used with risk maps to prioritize areas that may need to receive assistance in preventing a potential outbreak. For example, in areas where epidemic cholera is a frequent occurrence, preventative measures will already be underway in anticipation of an outbreak (often on a seasonal basis). In these contexts, the DRM and rainfall forecasts can be used to inform planning and preparation activities. The cholera risk information provided by the DRM should also be used to intensify early control measures such as surveillance and reporting, strengthening healthcare systems, and community engagement. Using cholera risk information in this way can help to flatten the epidemic curve. The advantage of predicting conditions optimal for cholera to occur is an improved capability for the public health system to act in time to prevent disease outbreak, that is, to provide appropriate and timely infrastructure and introduce vaccination for the most vulnerable of the population.

Next, an exemplary disease risk model for predicting a risk of outbreak of COVID-19 is described in accordance with embodiments of the present disclosure. In particular, a time series analysis is utilized to determine the occurrence of coronavirus disease 2019 (COVID-19) in the human population through ambient air and dew point temperatures. Through heuristic data analysis, a temperature range of 17-24 degrees Celsius was identified as tolerable, showing a reduction in the reported COVID-19 cases within the human population. However, both extremely low and high air temperatures had comparable impacts on the count of COVID-19 cases within indoor spaces. Both ends of the ambient temperature spectrum led to a migration of human activity towards indoors, increasing the likelihood of exposure to recirculated air. Conversely, colder temperatures contribute to the aerosolization of the virus in the outdoor air, thereby resulting in a higher incidence of human COVID-19 cases. Nonetheless, it is important to note that while a correlation exists, it does not imply a causal relationship. Therefore, we present a broadly applicable hypothesis that outlines the dynamics of COVID-19 within the human population, which offers a mechanistic explanation for the influence of temperature (both ambient air and dew point) and is based on the possibility of the virus becoming aerosolized through particles present in both outdoor and indoor environments. Lower humidity levels in the surrounding air encourage the virus to become aerosolized, leading to the extended suspension of particles in the air over prolonged time periods. Ambient air characterized by an extremely low dew point temperature can be utilized to facilitate the aerosolization of the virus. Once aerosolized, severe acute respiratory syndrome Coronavirus-2 (SARS-CoV-2) has the potential to spread in both indoor and outdoor settings, particularly in colder regions. The dew point temperature corresponds to the moisture level in the air such that a decrease in the dew point temperature indicates a reduction in the moisture content of the air.

Based on this hypothesis, five variables can be employed to develop an exemplary predictive system: ambient air temperature, dew point temperature, population density, ethnicity, and household income. Ambient air temperatures falling within the range of tolerable can be regarded as having the minimal influence on the virus transmission among humans. Deviations below 17° C. or above 24° C. can be assessed by calculating the square root to ensure consistency in variance across the variable. Any deviation from the 17° C. to 24° C. range can be restricted to a maximum of 16° C., wherein any value surpassing 16° C. can be treated as 16° C. The difference between ambient air temperature and dew point temperature can be employed as a measure to assess the cold and dry characteristics of the air.

In this context, areas with cold climates were identified as those encountering temperatures below freezing for three or more months. The daily calculation of the difference between ambient air temperature and dew point temperature was carried out over a two-week period prior to risk score prediction. Subsequently, these daily variations were influenced by the presence of negative dew point temperatures, with negative values represented as one and positive values as zero. Thus, an exemplary method characterized the cold and dry climatic conditions in regions marked by negative dew point temperatures. Classification was implemented on a scale ranging from 0 (lowest) to 4 (highest), where a risk score of 0 denoted zero risk when the dew point temperature was positive. A low-risk score was assigned when the value fell between 0 and 3.5. For values between 3.5 and 7, a medium risk score was designated. High risk corresponded to values ranging from 7 to 11.5, while values surpassing 11.5 were categorized as very high risk. Further the environmental factor was established by aggregating and subsequently normalizing both environmental parameters according to a 4:1 ratio. The socio-economic variable were further formulated using a heuristic methodology, assigning weights of 0.8, 0.1, and 0.1 to population density, ethnicity, and income, respectively. As all three variables were scaled between 0 and 1, the resulting socio-economic variable maintained the same scale. Population density was regarded as the pivotal socio-economic factor, quantified logarithmically on a scale spanning from 0 (minimum) to 4 (maximum). The second and third variables, ethnicity and household incomes, were assessed in relation to county-level ratios.

Via the disease risk model, the comprehensive risk of disease transmission can be computed as a product of the environmental and socio-economic risks together. As a result, social factors can solely contribute to determining the risk within the comfortable temperature range, while climatic variables impact the transmission rate beyond that specific range.

Figure 5:
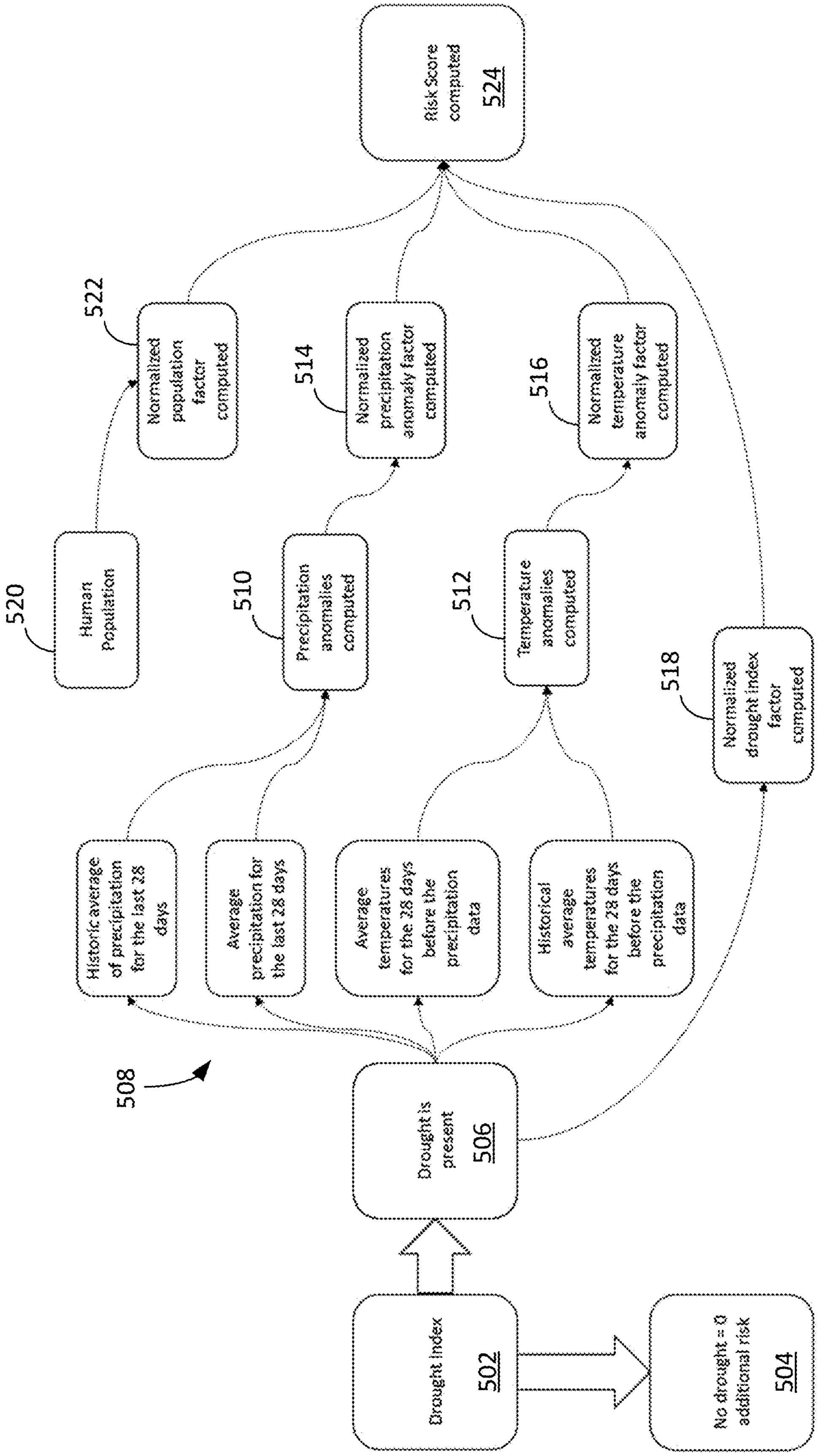
FIG. 5 shows an exemplary flowchart for a disease risk modeling process in accordance with various embodiments of the present disclosure.

FIG. 5 shows an exemplary flowchart of the disease risk model process for predicting a risk of cholera in accordance with various embodiments of the present disclosure. Here, a drought component of the disease risk model is used to predict the risk of cholera outbreak due to drought-like conditions. First, the model uses (502) a drought index from the most recent month as an input to determine if a region is experiencing a drought. If the region is not experiencing (504) a drought, then the model provides no additional risk to the final risk score for a region. If the region is experiencing (506) a drought, then the model uses (508) measures of precipitation from the last 28 days and the historical average of precipitation from the last 28 days as inputs to compute (510) the precipitation anomalies from the last 28 days. The model will do the same for temperatures from the 28 days before the precipitation data, with both recent and historic data being used as inputs, to compute (512) the temperature anomalies from the previous 28-day period. If the temperature anomalies are positive, then there will be an increased risk of cholera outbreak. If the precipitation anomalies are negative, then there will also be an increased risk of cholera outbreak.

The precipitation and temperature anomalies and drought index are normalized (514, 516, 518) so that a final risk score may be computed (524) by the disease risk model. As such, the more extreme the anomaly or drought, the higher the normalized risk factor will be. A normalized risk factor is also used (520-522) for the population in the region, with higher population returning a higher normalized risk factor. The normalized risk factors for the drought index, temperature anomalies, precipitation anomalies, and population are then added together to return (524) the final risk score.

Figure 6:
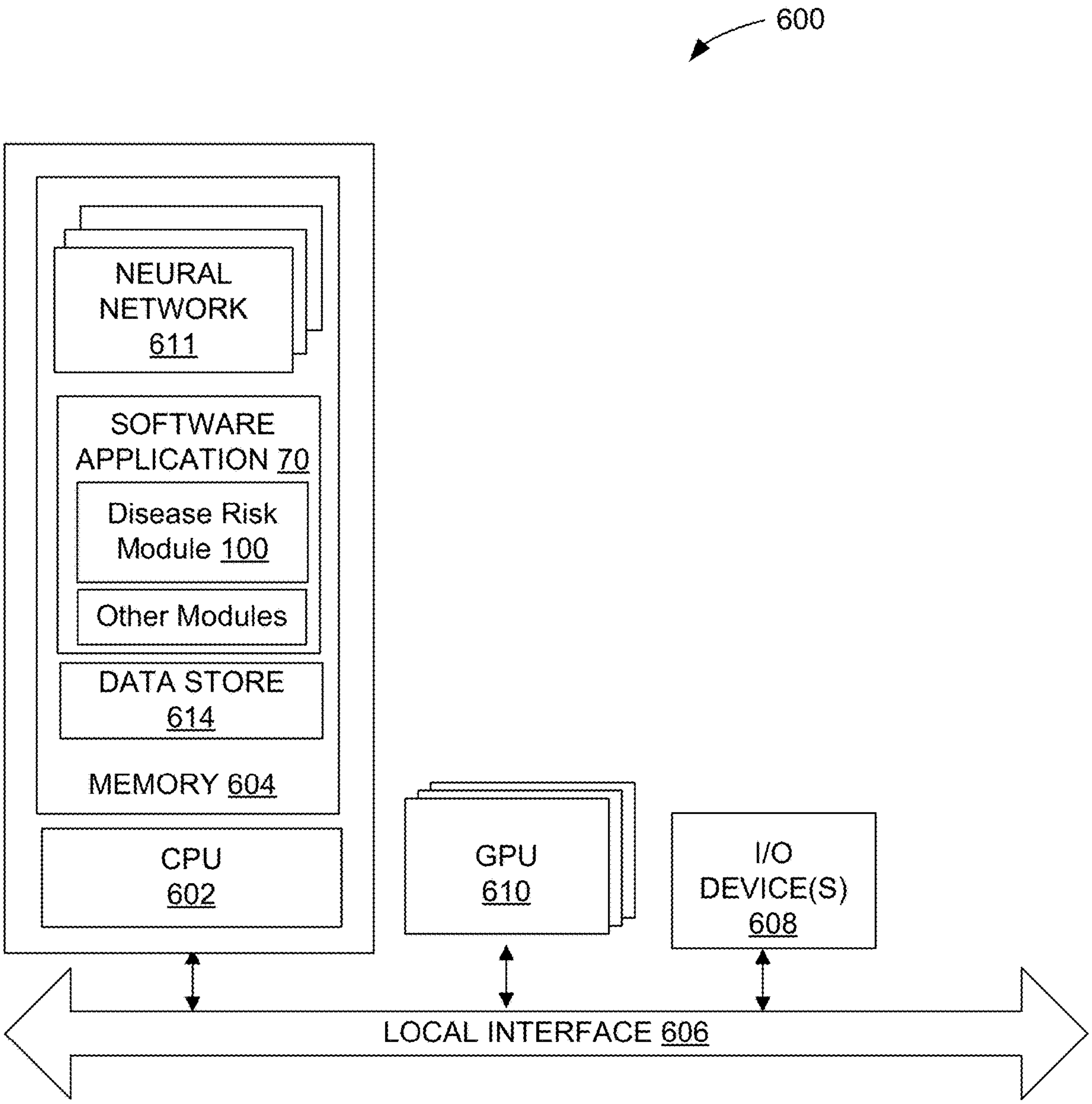
FIG. 6 shows a schematic block diagram of a computing device that can be used to implement various embodiments of the present disclosure.

Next, FIG. 6 depicts a schematic block diagram of a computing device 600 that can be used to implement various embodiments of the present disclosure, such as a prediction server 50. An exemplary computing device 600 includes at least one processor circuit, for example, having a processor (CPU) 602 and a memory 604, both of which are coupled to a local interface 606, and one or more input and output (I/O) devices 608. The local interface 606 may comprise, for example, a data bus with an accompanying address/control bus or other bus structure as can be appreciated. The computing device 600 further includes Graphical Processing Unit(s) (GPU) 610 that are coupled to the local interface 606 and may utilize memory 604 and/or may have its own dedicated memory. The CPU and/or GPU(s) can perform various operations such as image enhancement, graphics rendering, image/video processing, recognition (e.g., text recognition, object recognition, feature recognition, etc.), image stabilization, machine learning, filtering, image classification, and any of the various operations described herein.

Stored in the memory 604 are both data and several components that are executable by the processor 602. In particular, stored in the memory 604 and executable by the processor 602 are code for implementing one or more neural networks 611 (e.g., artificial and/or convolutional neural network models) and a software application 70 (e.g., using the neural network models 611) for building disease risk model(s) and predicting outbreaks and/or transmissions of one or more diseases. Accordingly, the software application can include a disease risk module 100 in addition to other modules in accordance with the present disclosure. Also stored in the memory 604 may be a data store 614 and other data. The data store 614 can include an electronic repository or database relevant to environmental and social risk factors. In addition, an operating system may be stored in the memory 604 and executable by the processor 602. The I/O devices 608 may include input devices, for example but not limited to, a keyboard, mouse, etc. Furthermore, the I/O devices 608 may also include output devices, for example but not limited to, a printer, display, etc.

Certain embodiments of the present disclosure can be implemented in hardware, software, firmware, or a combination thereof. If implemented in software, the logic or functionality for building disease risk model(s) and predicting outbreaks and/or transmissions of one or more diseases is implemented in software or firmware that is stored in a memory and that is executed by a suitable instruction execution system. If implemented in hardware, such logic or functionality can be implemented with any or a combination of the following technologies, which are all well known in the art: discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Also, any logic or application described herein that includes software or code can be embodied in any non-transitory computer-readable medium for use by or in connection with an instruction execution system such as a processor in a computer system or other system. In this sense, the logic can include statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. Moreover, a collection of distributed computer-readable media located across a plurality of computing devices (e.g., storage area networks or distributed or clustered filesystems or databases) may also be collectively considered as a single non-transitory computer-readable medium.

The computer-readable medium can include any one of many physical media such as magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium can be a random-access memory (RAM) including static random-access memory (SRAM) and dynamic random-access memory (DRAM), or magnetic random-access memory (MRAM). In addition, the computer-readable medium can be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

Therefore, at least the following is claimed:

1. A method comprising:

acquiring, by a computing device, environmental risk factor data, wherein the environmental risk factor data corresponds to a particular geographic region;

acquiring, by the computing device, social risk factor data associated with the particular disease, wherein the social risk factor corresponds to the particular geographic region;

receiving, by the computing device, a first input specifying a particular disease;

receiving, by the computing device, a second input specifying a first lead time in the future;

receiving, by the computing device, a third input specifying a second lead time in the future, wherein the second lead time is less than the first lead time;

selecting, by the computing device, subsets of the environmental risk factor data and the social risk factor data that are associated with the particular disease;

classifying each subset of the environmental risk factor data and the social risk factor data as a layer of clustered data, each layer assigned a measurement scale of values that are common between the different layers;

assigning an integer value to each layer of clustered data based on the common measurement scale of values;

applying, by the computing device, a prediction algorithm to the selected environmental and social risk factor data different layers to generate a disease risk model for generating at least a trigger prediction and a transmission prediction for a disease-causing pathogen at the particular geographic region, wherein each of the selected environmental risk factor data and the selected social risk factor data layers are assigned a weight based according to influence of the underlying data on the particular disease;

wherein the trigger prediction is a prediction of a disease outbreak at the particular geographic region at a first defined time period in the future corresponding to the first lead time;

wherein the transmission prediction is a prediction of a human-to-human transmission of the disease-causing pathogen at the particular geographic region at a second defined time period in the future corresponding to the second lead time;

generating, by the computing device, the trigger prediction by applying the disease risk model to a forecast of data for the first lead lime for the particular geographic region in the future;

generating, by the computing device, the transmission prediction by applying the disease risk model to the transmission prediction for the second lead lime for the particular geographic region in the future;

computing, by the computing device, a trigger prediction score and a transmission prediction score for a plurality of pixels of a risk map, wherein the plurality of pixels correspond to the particular geographic region; and generating, by the computing device, the risk map comprising the plurality of pixels, wherein the risk map indicates a likelihood of an outbreak and spread of the particular disease in the particular geographic region in the first and second defined periods.

2. The method of claim 1, wherein the forecast of data comprises a weather forecast for the particular geographic region.

3. The method of claim 1, wherein the first lead time or the second lead time comprises at least three weeks in the future.

4. The method of claim 1, wherein the environmental risk factor data comprises precipitation, air temperature, dew point temperature, air quality, sunlight, salinity, relative humidity, sea surface temperature, coastal location, or nutrients data.

5. The method of claim 1, wherein the social risk factor data comprises human mobility, population density, water infrastructure, economic stability, age demographic, population diversity, housing conditions, sanitation infrastructure, or behavioral data for the particular geographic region.

6. The method of claim 1, wherein the particular disease comprises cholera.

7. The method of claim 1, wherein the particular disease comprises COVID-19.

8. The method of claim 1, wherein the particular disease comprises a virus, bacteria, fungi, or a parasite.

9. A system of infection prevention data analysis comprising:

at least one processor; and memory configured to communicate with the at least one processor, wherein the memory stores instructions that, in response to execution by the at least one processor, cause the at least one processor to perform operations comprising:

acquiring environmental risk factor data, wherein the environmental risk factor data corresponds to a particular geographic region;

acquiring social risk factor data, wherein the social risk factor corresponds to the particular geographic region;

receiving a first input specifying a particular disease;

receiving a second input specifying a first lead time in the future;

receiving a third input specifying a second lead time in the future, wherein the second lead time is less than the first lead time;

selecting subsets of the environmental risk factor data and the social risk factor data that are associated with the particular disease;

classifying each subset of the environmental risk factor data and the social risk factor as a layer of clustered data, each layer assigned a measurement scale of values that are common between the different layers;

assigning an integer value to each layer of clustered data based on the common measurement scale of values;

applying a prediction algorithm to the environmental and social risk factor data different layers to generate a disease risk model for generating at least a trigger prediction and a transmission prediction for a disease-causing pathogen at the particular geographic region, wherein each of the selected environmental risk factor data and the selected social risk factor data layers are assigned a weight based according to influence of the underlying data on the particular disease;

wherein the trigger prediction is a prediction of a disease outbreak at the particular geographic region at a first defined time period in the future corresponding to the first lead time;

wherein the transmission prediction is a prediction of a human-to-human transmission of the disease-causing pathogen at the particular geographic region at a second defined time period in the future corresponding to the second lead time;

generating the trigger prediction by applying the disease risk model to a forecast of data for a first lead time for the particular geographic region; and generating the transmission prediction by applying the disease risk model to the transmission prediction for a second lead time for the particular geographic region in the future;

computing a trigger prediction score and a transmission prediction score for a plurality of pixels of a risk map, wherein the plurality of pixels correspond to the particular geographic region; and generating the risk map comprising the plurality of pixels, wherein the risk map indicates a likelihood of an outbreak and spread of the particular disease in the particular geographic region in the first and second defined time periods in the future.

10. The system of claim 9, wherein the forecast of data comprises a weather forecast for the particular geographic region.

11. The system of claim 9, wherein the first lead time or the second lead time comprises at least three weeks in the future.

12. The system of claim 9, wherein the particular disease comprises cholera.

13. The system of claim 9, wherein the particular disease comprises COVID-19.

14. A non-transitory, computer-readable medium comprising machine-readable instructions that, when executed by a processor of a computing device, cause the computing device to at least:

acquire environmental risk factor data, wherein the environmental risk factor data corresponds to a particular geographic region;

acquire social risk factor data, wherein the social risk factor corresponds to the particular geographic region;

receive a first input specifying a particular disease;

receive a second input specifying a first lead time in the future;

receive a third input specifying a second lead time in the future, wherein the second lead time is less than the first lead time;

select subsets of the environmental risk factor data and the social risk factor data that are associated with the particular disease;

classify each subset of the environmental risk factor data and the social risk factor as a layer of clustered data, each layer assigned a measurement scale of values that are common between the different layers; assign an integer value to each layer of clustered data based on the common measurement scale of values;

apply a prediction algorithm to the selected environmental and social risk factor data different layers to generate a disease risk model for generating at least a trigger prediction and a transmission prediction for a disease-causing pathogen at the particular geographic region, wherein each of the selected environmental risk factor data and the selected social risk factor data layers are assigned a weight based according to influence of the underlying data on the particular disease;

wherein the trigger prediction is a prediction of a disease outbreak at the particular geographic region at a first defined time period in the future corresponding to the first lead time;

wherein the transmission prediction is a prediction of a human-to-human transmission of the disease-causing pathogen at the particular geographic region at a second defined time period in the future corresponding to the second lead time;

generate the trigger prediction by applying the disease risk model to a forecast of data for a first lead time for the particular geographic region in the future;

generate the transmission prediction by applying the disease risk model to the transmission prediction for the second lead time for the particular geographic region in the future;

compute a trigger prediction score and a transmission prediction score for a plurality of pixels of a risk map, wherein the plurality of pixels correspond to the particular geographic region; and generate the risk map comprising the plurality of pixels, wherein the risk map indicates a likelihood of an outbreak and spread of the particular disease in the particular geographic region in the first and second defined time periods in the future corresponding to the first lead time.

15. The non-transitory, computer-readable medium of claim 14, wherein the first lead time or the second lead time comprises at least three weeks in the future.

16. The non-transitory, computer-readable medium of claim 14, wherein the forecast of data comprises a weather forecast for the particular geographic region.

17. The non-transitory, computer-readable medium of claim 14, wherein the particular disease comprises cholera or COVID-19.

18. The method of claim 1, wherein the risk map includes the particular geographic region in addition to one or more other geographic regions, wherein the geographic regions having a higher risk of the outbreak and spread of the particular disease are displayed in a different color or shade than other geographic regions having a lower risk of the outbreak and spread of the particular disease, wherein for each geographic region, the disease risk model is applied to certain environmental and social risk factor data associated with each geographic region and the particular disease to compute the trigger prediction score and the transmission prediction score for each geographic region.

19. The system of claim 9, wherein the risk map includes the particular geographic region in addition to one or more other geographic regions, wherein the geographic regions having a higher risk of the outbreak and spread of the particular disease are displayed in a different color or shade than other geographic regions having a lower risk of the outbreak and spread of the particular disease, wherein for each geographic region, the disease risk model is applied to certain environmental and social risk factor data associated with each geographic region and the particular disease to compute the trigger prediction score and the transmission prediction score for each geographic region.

20. The non-transitory, computer-readable medium of claim 14, wherein the risk map includes the particular geographic region in addition to one or more other geographic regions, wherein the geographic regions having a higher risk of the outbreak and spread of the particular disease are displayed in a different color or shade than other geographic regions having a lower risk of the outbreak and spread of the particular disease, wherein for each geographic region, the disease risk model is applied to certain environmental and social risk factor data associated with each geographic region and the particular disease to compute the trigger prediction score and the transmission prediction score for each geographic region.

* * * * *